(12) United States Patent
Ho et al.

(10) Patent No.: US 7,632,804 B2
(45) Date of Patent: *Dec. 15, 2009

(54) DIETARY PRODUCTS COMPRISING ONE OR MORE OF γ-POLYGLUTAMIC ACID (γ-PGA, H FORM) AND γ-POLYGLUTAMATES FOR USE AS NUTRITION SUPPLEMENTS

(75) Inventors: Guan-Huei Ho, Richmond Hill (CA); Tou-Hsiung Yang, Taichung Hsien (TW); Jeng Yang, Taichung Hsien (TW)

(73) Assignee: Tung Hai Biotechnology Corporation, Taichung Hsien (TW)

( * ) Notice: Subject to any disclaimer, the term of this patent is extended or adjusted under 35 U.S.C. 154(b) by 48 days.

This patent is subject to a terminal disclaimer.

(21) Appl. No.: 11/223,037

(22) Filed: Sep. 12, 2005

(65) Prior Publication Data

US 2006/0257468 A1    Nov. 16, 2006

(30) Foreign Application Priority Data

May 16, 2005    (TW) ............................. 94115737 A

(51) Int. Cl.
*A61K 38/01* (2006.01)
(52) U.S. Cl. ......................................... 514/2
(58) Field of Classification Search ........................ None
See application file for complete search history.

(56) References Cited

U.S. PATENT DOCUMENTS

| | | | |
|---|---|---|---|
| 4,179,337 | A | 12/1979 | Davis et al. |
| 4,261,973 | A | 4/1981 | Lee et al. |
| 4,294,753 | A | 10/1981 | Urist |
| 4,301,144 | A | 11/1981 | Iwashita et al. |
| 4,434,094 | A | 2/1984 | Seyedin et al. |
| 4,455,256 | A | 6/1984 | Urist |
| 4,816,442 | A | 3/1989 | McPherson et al. |
| 4,830,847 | A | 5/1989 | Benedict et al. |
| 4,888,193 | A | 12/1989 | Konno et al. |
| 5,447,732 | A * | 9/1995 | Tanimoto et al. ............... 426/74 |
| 6,251,422 | B1 * | 6/2001 | Tanimoto et al. ............ 424/442 |
| 6,271,278 | B1 * | 8/2001 | Park et al. .................... 521/150 |

FOREIGN PATENT DOCUMENTS

| | | |
|---|---|---|
| EP | 0 512 844 | 11/1992 |
| EP | 0 838 160 | 4/1998 |
| JP | 05-316999 | 12/1993 |
| JP | 2003-61575 | 3/2003 |

OTHER PUBLICATIONS

Tanimoto et al. "Natto mucilage containing poly-gamma-glutamic acid increases soluble calcium in the rat small intestine." Biosci. Biotechnol. Biochem., 2001, 65, 516-21.*
Shih et al. "Antifreeze activities of poly(gamma-glutamic acid) produced by *Bacillus licheniformis*." Biotech. Let., 2003, 25, 1709-12.*
Gonzales et al. "Synthesis and swelling characterizations of a poly(gamma-glutamic acid) hydrogel." J. Pol. Sci. A, 1996, 34, 2019-27.*
Shih & Van "The production of poly-(gamma-glutamic acid) from microorganisms and its various applications." Biores. Tech., 2001, 79, 207-25.*
Vedan International gamma-PGA product information (http://www.vedaninternational.com/products/PGArelease.htm).*
Athawale & Lele, Recent Trends in Hydrogels Based on Starch-.graft-Acrylic Acid: A Review, Starch, 2001, 53, 7-13.*
http://www.thefreedictionary.com/nutriment.*
Partial European Search Report dated Dec. 22, 2005, in counterpart European Application No. 05252997.1.
Patent Abstracts of Japan for JP06032742 published Feb. 8, 1994.
Patent Abstracts of Japan for JP05095767 published Apr. 20, 1993.
Patent Abstracts of Japan for JP2000270811 published Oct. 3, 2000.
Ohta et al., "Two Forms of Transforming Growth Factor-β Distinguished by Multipotential Haematopoietic Progenitor Cells", Nature, vol. 329, No. 8, pp. 539-541, (1987).
Rook et al., "Effects of Transforming Growth Factor β on the Functions of Natural Killer Cells: Depressed Cytolytic Activity and Blunting of Interferon Responsiveness", The Journal of Immunology, vol. 136, No. 10, pp. 3916-3920, (1986).
Vale et al., "Purification and Characterization of an FSH Releasing Protein from Porcine Ovarian Follicular Fluid", Nature, vol. 321, No. 19, pp. 776-779, (1986).
Totsuka et al, "A Novel Action of Activin A: Stimulation of Insulin Secretion in Rat Pancreatic Islets", Biochemical and Biophysical Research Communications, vol. 156, No. 1, pp. 335-339, (1988).
Yu et al., "Importance of FSH-Releasing Protein and Inhibin in Erythrodifferentiation", Nature, vol. 330, 24/31, pp. 765-767, (1987).
Joyce et al., "Transforming Growth Factor-β and the Initiation of Chondrogenesis and Osteogenesis in the Rat Femur", The Journal of Cell Biology, vol. 110, pp. 2195-2207, (1990).
Kubota et al., "Production of poly(γ-glutamic Acid) by *Bacillus subtilis* F-2-01", Biosci. Biotech. Biochem., vol. 57, No. 7, pp. 1212-1213, (1993).
Ogawa et al., "Efficient Production of γ-Polyglutamic Acid by *Bacillus subtilis (natto)* in Jar Fermenters", pp. 1684-1687, (1997).
Weinreb et al., "Different Pattern of Alkaline Phosphatase, Osteopontin, and Osteocalcin Expression in Developing Rat Bone Visualized by In Situ Hybridization", Journal of Bone and Mineral Research, vol. 5, No. 8, pp. 831-841, (1990).
Yao et al., "Temporal Changes in Matrix Protein Synthesis and mRNA Expression During Mineralized Tissue Formation by Adult Rat Bone Marrow Cells in Culture", Journal of Bone and Mineral Research, vol. 9, No. 2, pp. 231-240, (1994).

(Continued)

*Primary Examiner*—Cecilia Tsang
*Assistant Examiner*—Christina Bradley
(74) *Attorney, Agent, or Firm*—Finnegan, Henderson, Farabow, Garrett & Dunner, L.L.P.

(57) ABSTRACT

The present invention relates to a dietary product comprising γ-polyglutamic acid (γ-PGA, H form), and/or one or more of its salts (i.e., γ-polyglutamate in $Na^+$ form, γ-polyglutamate in $K^+$ form, γ-polyglutamate in $NH_4^+$ form, γ-polyglutamate in $Mg^{++}$ form, and γ-polyglutamate in $Ca^{++}$ form) for use as a nutrition supplement.

7 Claims, 6 Drawing Sheets

OTHER PUBLICATIONS

Herbertson et al., "Dexamethasone Alters the Subpopulation Make-Up of Rat Bone Marrow Stromal Cell Cultures", Journal of Bone and Mineral Research, vol. 10, No. 2, pp. 285-294, (1995).

Havenstein et al., "Growth, Livability, and Feed Conversion of 1957 vs 1991 Broilers When Fed "Typical" 1957 and 1991 Broiler Diets", Poultry Science, vol. 73, pp. 1785-1794, (1994).

Pansu et al., "Effect of Ca Intake on Saturable and Nonsaturable Components of Duodenal Ca Transport", The American Journal of Physiology, vol. 240, No. 1, pp. G32-G37, (1981).

Ganss et al., "Bone Sialoprotein", Critical Reviews of Oral Biology & Medicine, vol. 10, (3 pages), (1999).

Office Action for Taiwan counterpart to U.S. Appl. No. 11/223,037 issued on Nov. 2, 2006, and partial English translation thereof.

* cited by examiner

γ - poly - glutamic acid (or γ-PGA)

Repeating unit of M(I) γ- poly - (L) - glutamate
[M(I) γ- (L) - PGA]

Repeating unit of M(II)$_{1/2}$ γ-poly - (D) - glutamate
[M(II)$_{1/2}$ γ- (D) - PGA]

US 7,632,804 B2

DIETARY PRODUCTS COMPRISING ONE OR MORE OF γ-POLYGLUTAMIC ACID (γ-PGA, H FORM) AND γ-POLYGLUTAMATES FOR USE AS NUTRITION SUPPLEMENTS

TECHNICAL FIELD OF THE INVENTION

The present invention relates to a dietary product comprising γ-polyglutamic acid (γ-PGA, H form), γ-polyglutamate in $Na^+$ form, γ-polyglutamate in $K^+$ form, γ-polyglutamate in $NH_4^+$ form, γ-polyglutamate in $Mg^{++}$ form or γ-polyglutamate in $Ca^{++}$ form, or a mixture thereof, which enhances the absorption of calcium in the intestine and by the bone. More specifically, the present invention relates to complex adsorbents or nutrition supplements comprising γ-polyglutamic acid (γ-PGA, H form), γ-polyglutamate in $Na^+$ form, γ-polyglutamate in $K^+$ form, γ-polyglutamate in $NH_4^+$ form, γ-polyglutamate in $Mg^{++}$ form or γ-polyglutamate in $Ca^{++}$ form, or a mixture thereof for use in food or an animal feed composition for facilitating calcium absorption, preventing osteoporosis and reducing calcium loss, maintaining bone strength and improving the growth and healthy condition.

TECHNICAL BACKGROUND AND PRIOR ART

"Transforming growth factor-beta" (TGF-β) represents a family of proteins, which are evolutionarily highly conserved, and affect a broad spectrum of cell types. TGF-β was first identified as a factor, which permitted anchorage-independent growth of primary cell cultures. In vivo, TGF-β promotes the deposition of connective tissue, and induces cell growth of mesenchymal origin. TGF-β affects the proliferation and differentiation of the cells of immune system including hematopoietic stem cells (see Ohta et al., Nature (1987), 329:539) and NK cells (see Rook et al., J. Immunol. (1986) 136:3916). TGF-β may also be administered to suppress hyperproliferation, such as cancer and leukemia (see U.S. Pat. No. 4,816,442).

"Bone morphogenetic protein (BMP)" was extracted from demineralized bone using urea or guanidine hydrochloride and reprecipitated according to the disclosures in the U.S. Pat. Nos. 4,294,753 and 4,455,256. Seyedin and Thomas reported in U.S. Pat. No. 4,434,094 the partial purification of a bone generation-stimulating, bone-derived protein by extraction with chaotropic agents, and recovery of the activity from a fraction adsorbed to CMC at pH 4.8. The new protein fraction was termed "osteogenic factor" and was characterized as having a molecular weight below about 30,000 daltons.

Activins are dimeric proteins, representing a family of proteins structurally related to TGF-β1, and similar to inhibins. Inhibins are heterodimers of the activin subunits and a separate activin subunit. Activins have been shown to stimulate the release of follicle stimulating hormone (see W. Vale et al., Nature (1986), 321:776-79), insulin secretion from pancreatic islets (see Y. Totsuka et al., Biochem. & Biophys. Res. Comm. (1988) 156:335-39), and erythroid and multipotential progenitor cell colony formation in bone marrow culture (see J. Yu et al., Nature (1987) 330:765-67) and induce formation of endochondral bone in vivo (see M. E. Joyce et al., J. Cell Biol. (1990) 110:2195-2207).

Bone sialoprotein (BSP) is a highly glycosylated and sulphated phosphoprotein that is found exclusively in mineralized connective tissues. Polyglutamic acid motifs with the ability to bind hydroxyapatite and cell-surface integrins. BSP has the biophysical and chemical functionalities of a bone nucleator. The hydroxyapatite-binding polyglutamic acid sequence provide bifunctional entites through which BSP may mediate the targeting and attachment of normal and metastasizing cells to the bone surface (see Ganes et al., Bone Sialoprotein, Critical Reviews in Oral Biology and Medicine, 10(1):79-98).

There are several references in the art related to proteins modified by covalent conjugation to polymers, to alter the solubility, antigenicity and biological clearance of the protein (see U.S. Pat. Nos. 4,261,973, 4,301,144, 4,179,337, and 4,830,847). CA2102808, published on 11 Nov. 1992, disclosed a composition comprising a bone growth factor and a targeting molecule having affinity for a tissue of interest, where the bone growth factor and targeting molecule are chemically conjugated to a cross-linker. The cross-linker is preferably a synthetic hydrophilic polymer. The molecules preferably have an affinity for bone. The bone growth factor is preferebly TGF-β, Activin, bone morphogenic protein (BMP), or bone sialoprotein (BSP). The tissue of interest includes bone, cartilage, or other tissues or cell types to which bone growth factors may be targeted. The compositions are intended for use in augmentation of bone formation and repairing or treating bone loss, which are normally found in osteoporosis, osteoarthritis, or age-related loss of bone mass.

It was known that the absorption of calcium in human body basically followed two paths: the active transport and the passive transport. The active transport path is mainly controlled by the regulation of vitamin D and various hormones, in which calcium is absorbed in the upper small intestine against a concentration gradient, while in the passive transport path, calcium in the lower small intestine is absorbed following a concentration gradient. The ratio of the passive transport to the lower small intestine is overwhelmingly high when the soluble calcium is available in abundant. The active transport path cannot rise above a certain amount even if the concentration of soluble calcium increases, while the passive transport rises as the concentration of soluble calcium in the intestine increases. The rate of calcium absorption in the intestines has been reported to be in the range of 10-50%. Casein phosphopeptide (CPP), an enzymatic degradation product of the milk protein casein in gut, accelerates the absorption of calcium (see U.S. Pat. No. 5,447,732 published on 5 Sep. 1995) by raising the concentration of soluble calcium in the small intestine. Calcium is maintained in a soluble state by the complex coordination of the phosphate groups of phosphoserine and carboxylate groups of the acidic amino acids contained in CPP.

CONTENT OF THE INVENTION

In this invention, a dietary product comprising γ-polyglutamic acid (γ-PGA, H form), γ-polyglutamate in $Na^+$ form, γ-polyglutamate in $K^+$ form, γ-polyglutamate in $NH_4^+$ form, γ-polyglutamate in $Mg^{++}$ form or γ-polyglutamate in $Ca^{++}$ form or a mixture thereof is used as a nutrition supplement, which effectively solubilizes and stabilizes both calcium and magnesium through the formation of complexes and effectively make calcium and magnesium more bioavailable when used in food or feed composition.

DETAILED DESCRIPTION OF THE INVENTION

Figure 1:
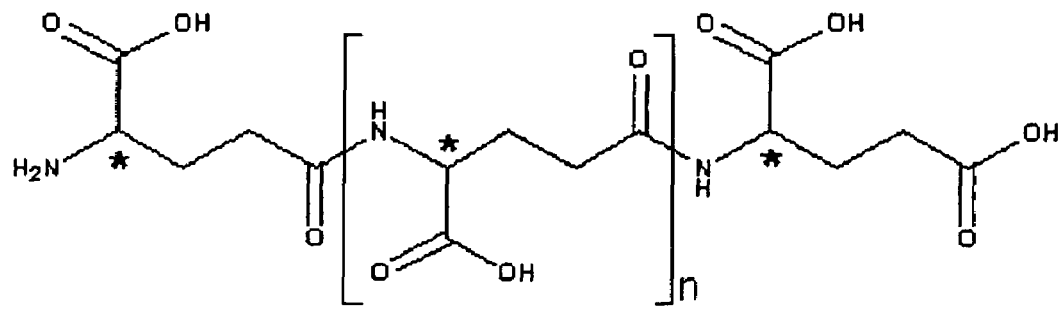
FIG. 1 shows the chemical structure of γ-polyglutamic acid (γ-PGA, H form) (A), γ-polyglutamate in K$^+$ form, γ-polyglutamate in Na$^+$ form, and γ-polyglutamate in NH$_4^+$ form (B), and γ-polyglutamate in Ca$^{++}$ form and γ-polyglutamate in Mg$^{++}$ form (C) (M(I)=K$^+$, Na$^+$, or NH$_4^+$; M(II)=Ca$^{++}$ or Mg$^{++}$).
Figure 1:
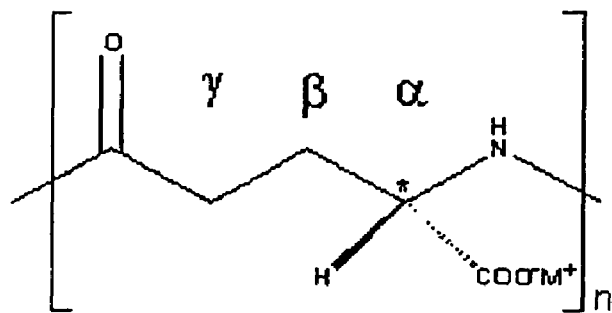
Figure 1:
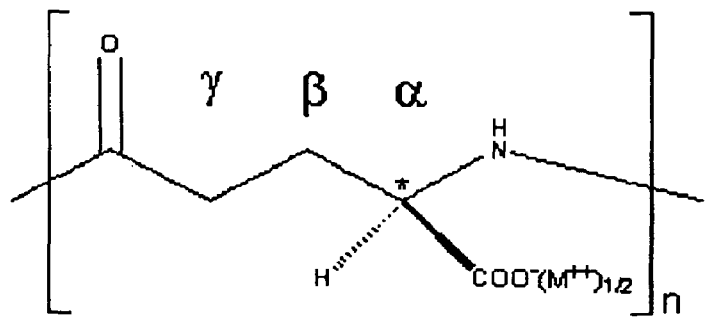
Figure 2:
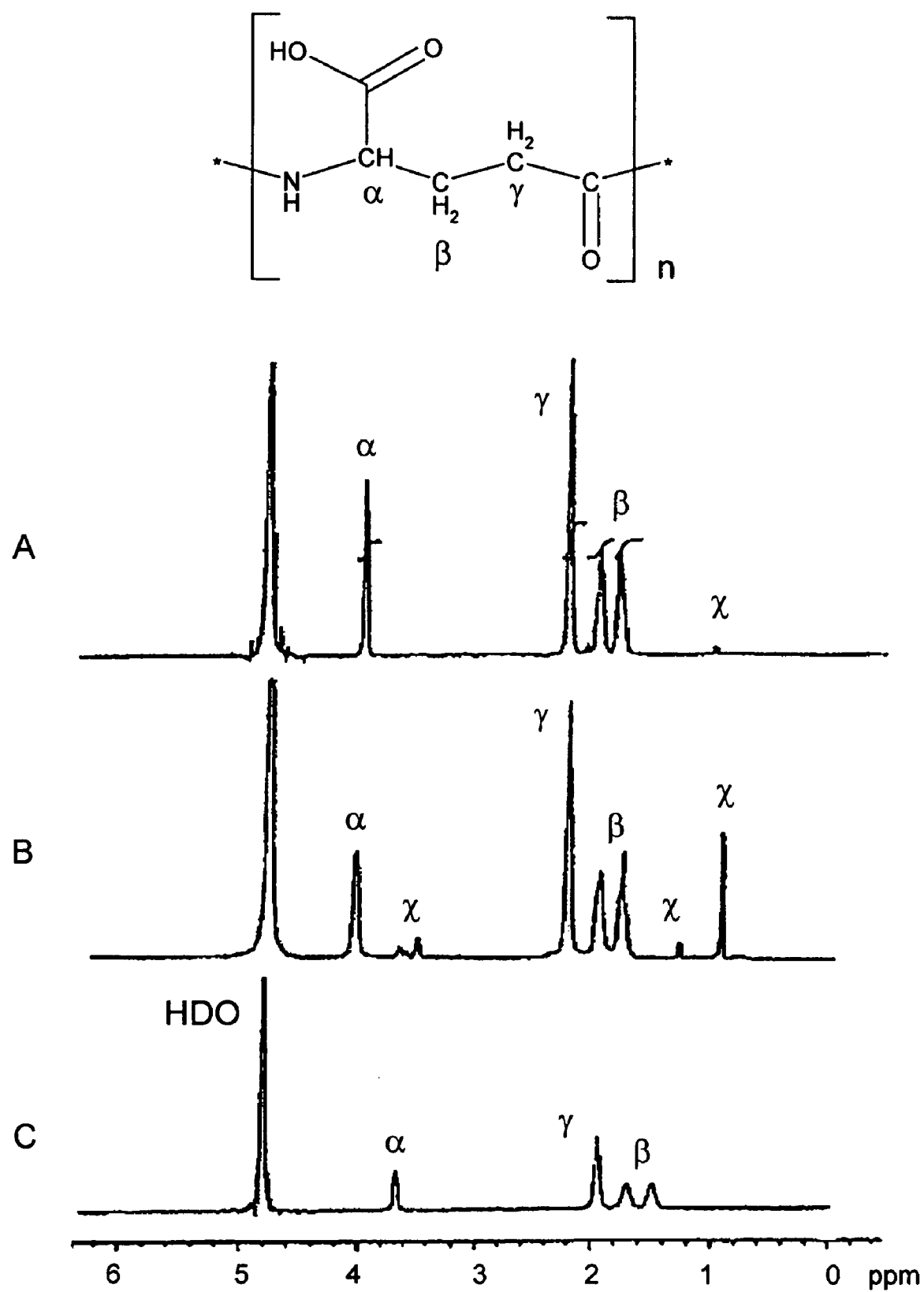
FIG. 2 shows 400 MHz $^1$H-NMR spectra of γ-polyglutamate in Na$^+$ form (A), γ-polyglutamate in K$^+$ form (B), and γ-polyglutamate in NH$_4^+$ form (C) in D$_2$O at neutral pH and temperature of 30° C. Chemical shift was measured in ppm units from the internal standard. X indicates impurity peak.
Figure 3:
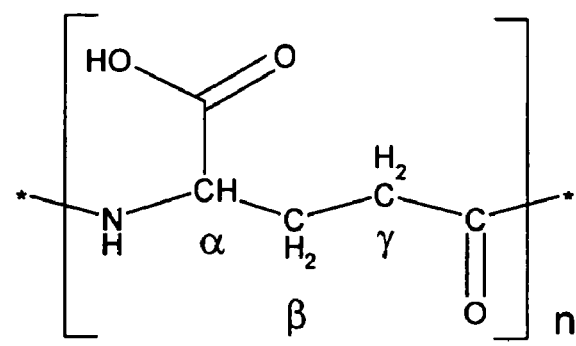
FIG. 3 shows $^{13}$C-NMR spectra of γ-polyglutamate in K$^+$ form (A), γ-polyglutamate in Na$^+$ form (B), γ-polyglutamate in Ca$^{++}$ form (C), and γ-polyglutamate in Mg$^{++}$ form (D) in D$_2$O at neutral pH and temperature of 30° C. Chemical shift was measured in ppm units from the internal reference.
Figure 3:
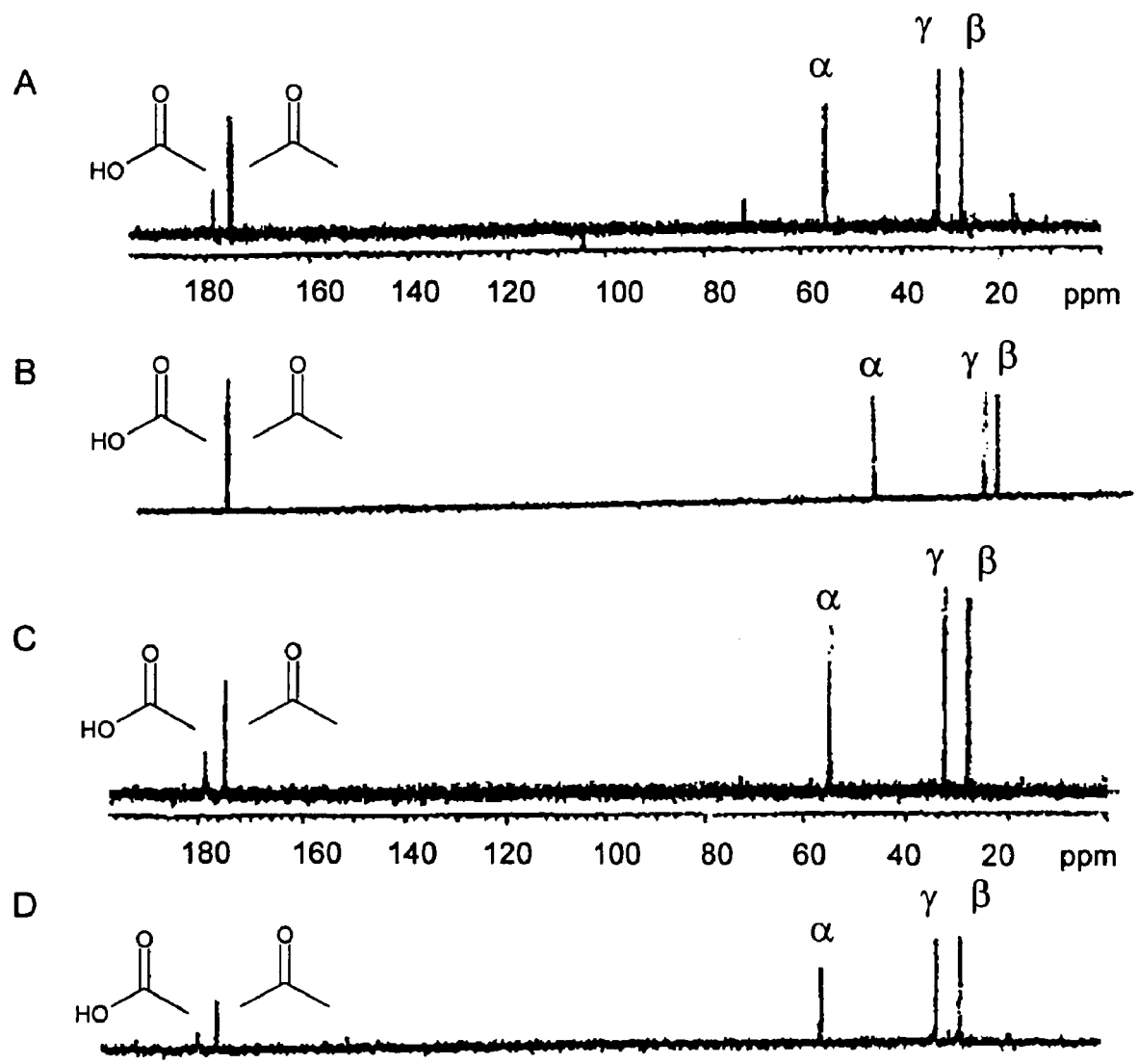
Figure 4:
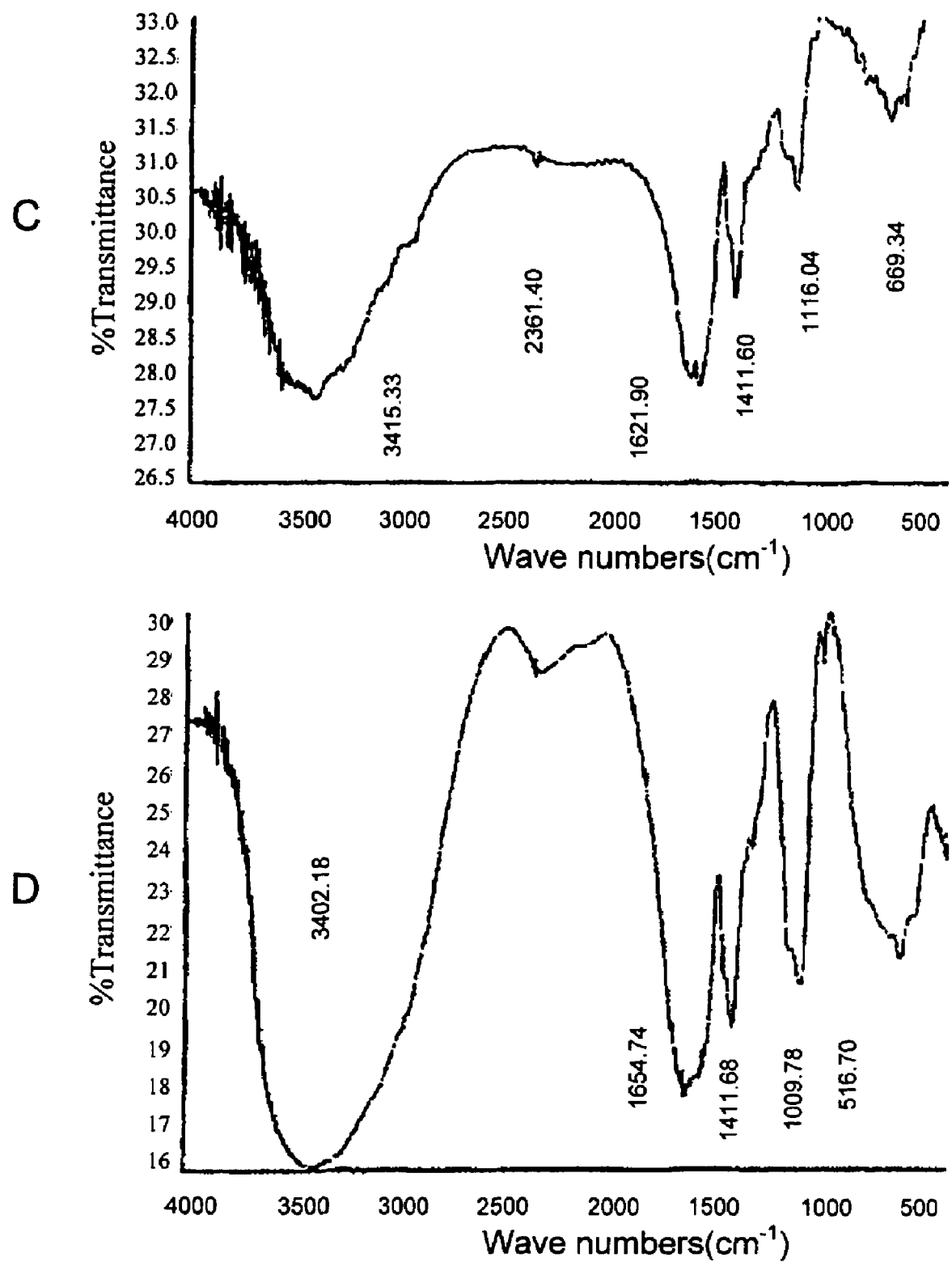
FIG. 4 shows infrared (FT-IR) absorption spectra of γ-polyglutamate in Ca$^{++}$ form (C) and γ-polyglutamate in Mg$^{++}$ form (D) in KBr pellet.
Figure 5:
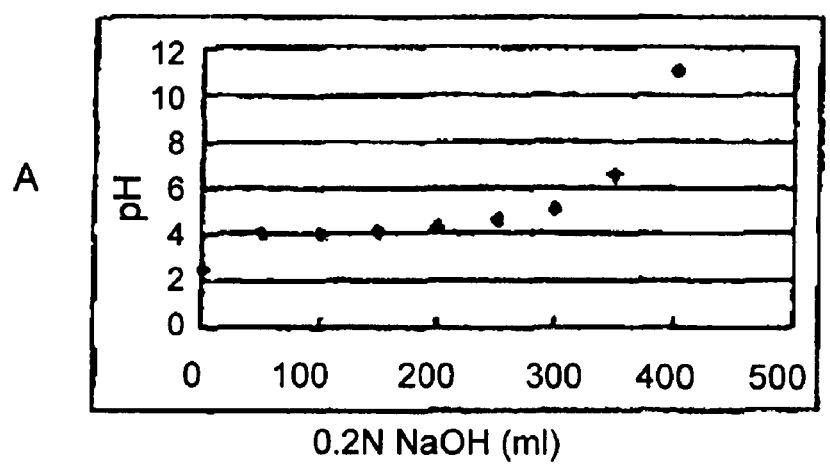
FIG. 5 shows pH-titration curves of γ-PGA with 0.2N NaOH (A), γ-PGA with Ca(OH)$_2$ (B), and γ-PGA with 5N NH$_4$OH(C) at 25° C.
Figure 5:
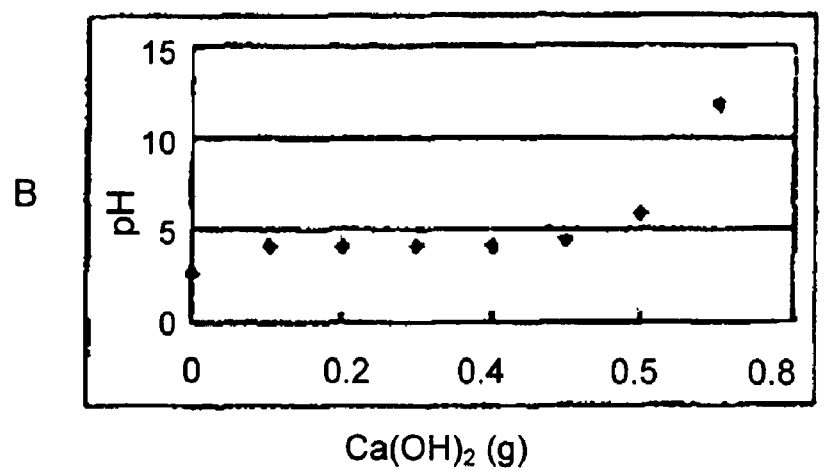
Figure 5:
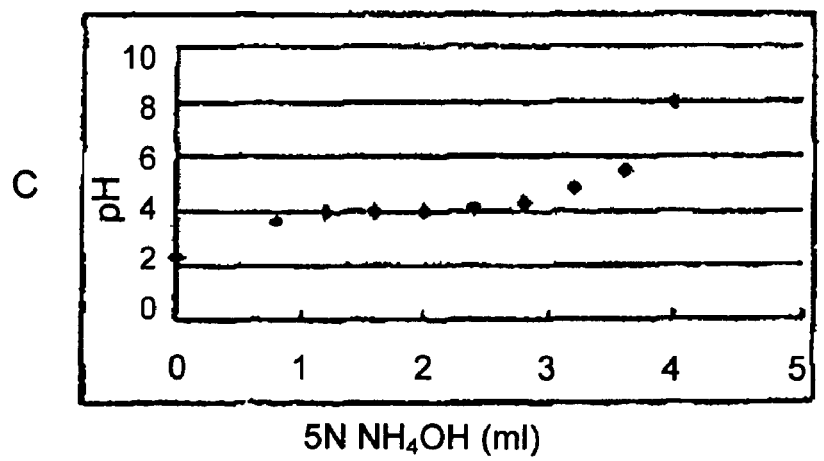

The present invention relates to a food or animal feed comprising γ-polyglutamic acid (γ-PGA, H form), γ-polyglutamate in Na$^+$ form, γ-polyglutamate in K$^+$ form, γ-polyglutamate in NH$_4^+$ form, γ-polyglutamate in Mg$^{++}$ form, or γ-polyglutamate in Ca$^{++}$ form or a mixture thereof for use as a nutritional supplement to facilitate the absorption of dietary calcium and the growth of osteoblast cells. γ-Polyglutamic acid (γ-PGA, H form) and γ-polyglutamates (Na$^+$, K$^+$, NH$_4^+$, Ca$^{++}$ and Mg$^{++}$ forms) are biodegradable, non-toxic biopolymers produced from L-glutamic acid via a submerge fermentation process (see H. Kubota et al., Production of Poly(γ-Glutamic Acid) by *Bacillus subtitlis* F-2-01, Biosci. Biotech. Biochem. 57(7), 1212-1213, 1993 and Y. Ogawa et. al., Efficient Production of γ-Polyglutamic Acid by *Bacillus subtilis* (natto) in Jar Fermentation, 61(10), 1684-1687, 1997). γ-Polyglutamates (Na$^+$, K$^+$, NH$_4^+$, Ca$^{++}$, and Mg$^{++}$ forms) possess excellent water absorption properties, form complex and have good coordination capacity for the metal ions of Ca$^{++}$, Mg$^{++}$, Zn$^{++}$, Mn$^{++}$, Se$^{++++}$ and Cr$^{+++}$, and their polyanionic properties are being explored for applications in solubilizing and stabilizing the above mentioned metal ions in aqueous systems. The molecular structures of γ-polyglutamic acid (γ-PGA) and γ-polyglutamates (Na$^+$, K$^+$, NH$_4^+$, Ca$^{++}$ Mg$^{++}$ forms) are shown in FIG. 1, the $^1$H-NMR, $^{13}$C-NMR, and FT-IR spectra are shown in FIGS. 2, 3, and 4, respectively. The spectral and analytical data are summarized in Table 1. The pH-titration curves are shown in FIG. 5

TABLE 1

| ITEM | H | Na$^+$ | K$^+$ | NH$_4^+$ | Ca$^{++}$ | Mg$^{++}$ |
|---|---|---|---|---|---|---|
| a. $^1$H-NMR(400 MHz, D$_2$O, 30° C.) Chemical shift in ppm: | | | | | | |
| α CH | | 3.98 | 4.00 | 3.68 | 4.18 | 4.08 |
| β CH$_2$ | | 1.98, 1.80 | 1.99, 1.80 | 1.68, 1.48 | 2.16, 1.93 | 2.05, 1.88 |
| γ CH$_2$ | | 2.19 | 2.19 | 1.93 | 2.38 | 2.31 |
| b. $^{13}$C-NMR(67.9 MHz, D$_2$O, 30° C.) Chemical shift in ppm; | | | | | | |
| α CH | | 56.43 | 62.21 | | 62.21 | 62.10 |
| β CH$_2$ | | 31.61 | 35.16 | | 36.17 | 35.11 |
| γ CH$_2$ | | 34.01 | 39.74 | | 39.68 | 39.60 |
| CO | | 182.21 | 182.11 | | 182.16 | 182.12 |
| COO$^-$ | | 182.69 | 185.46 | | 185.82 | 185.16 |
| a. FT-IR absorption (KBr), cm$^{-1}$ | | | | | | |
| C=O, Stretch | 1739 | | | | | |
| Amid I, N—H bending | | 1643 | | 1643 | 1622 | 1654 |
| Amide II, stretch | | 1585 | | | | |
| C=O, symmetric stretch | 1454 | 1402 | | 1395 | 1412 | 1411 |
| C—N, stretch | 1162 | 1131 | | 1139 | 1116 | 1089 |
| N—H, oop bending | 698 | 707 | | 685 | 669 | 616 |
| O—H, stretch | 3449 | 3436 | | 3443 | 3415 | 3402 |
| b. Thermal analysis: | | | | | | |
| Hydrated water | 0 | 10% | 42% | | 20% | 40% |
| Dehydration temperature, ° C. | | 109. | 139. | | 110 | 122 |
| T$_m$, ° C. | 206 | 160 | 193, 238 | 219 | — | 160. |
| T$_d$, ° C. | 209.8 | 340 | 341 | 223 | 335.7 | 331.8 |

γ-Polyglutamic acid (γ-PGA, H form) is a biopolymer of glutamic acid with a degree of polymerization ranging from 1,000 up to 20,000, and formed in only γ-peptide linkage between the glutamic moieties. γ-Polyglutamic acid (γ-PGA, H form) and γ-polyglutamates (Na$^+$, K$^+$, NH$_4^+$, Ca$^{++}$, and Mg$^{++}$ forms) contain a terminal amine and multiple α-carboxylic acid/carbooxylate groups. γ-Polyglutamic acid (γ-PGA, H form) and γ-polyglutamates (Na$^+$, K$^+$, NH$_4^+$, Ca$^{++}$ and Mg$^{++}$ forms) exist in several conformational states: α-helix, random coil, β-sheet, helix-coil transition region and enveloped aggregation, depending on the environmental conditions such as pH, ionic strength and other cationic species. With circular dichroism (CD), the amount of α-helical form present is usually measured as a function of magnitude of the spectra at 222 nm. Helix-coil transition takes place from about pH 3-5 for free form of γ-polyglutamic acid (γ-PGA, H form) in homogeneous, aqueous solution, and shift to a higher pH 5-7 for a bonded form. The transition from random coil to enveloped aggregation occurs when complex-coordination with certain divalent and some higher metallic ions through drastic conformational change of γ-PGA.

Our studies show that γ-polyglutamic acid (γ-PGA, H form) and γ-polyglutamates (Na$^+$, K$^+$, NH$_4^+$, Mg$^{++}$ and Ca$^{++}$ forms) effectively solubilize and stabilize both calcium and magnesium through formation of complexes, and effectively make calcium and magnesium more bioavailable when used in food or used in animal feed as a nutrition supplement.

γ-Polyglutamic acid (γ-PGA, H form) reacts with calcium salts and magnesium salts to form stable, water soluble calcium γ-polyglutamate and magnesium γ-polyglutamate, respectively. We found that these coordinated complexes, calcium γ-polyglutamate and magnesium γ-polyglutamate, are more absorbable and bioavailable according to in vitro cell culture study.

Metal adsorption onto γ-PGA involves two possible mechanisms: (A) direct interaction of metal ions with carboxylic sites and (B) retention of heavy metal counter-ions in mobile form by the electrostatic potential field created by the COO$^-$ groups. Besides, the interactions with the carboxylate groups, amide linkages may also provide weak interaction sites. In addition to the conformational structure and ionization of γ-PGA, it is also important to know the types of hydrolyzed metal species, which are present in an aqueous solution. The formation of a variety of different species may lead to different adsorption capacities of the metallic ions Osteoporosis and bone fracture are common metabolic diseases found in the elderly and in women after menopause. Dietary calcium is essential when considering calcium requirements in the elderly for prevention of osteoporosis conditions, or even increasing bone strength and bone mineral density. Osteoporosis is a disorder characterized by bone loss and is associated with an increased risk of bone fractures and back or joint pain. It is important for the prevention of osteoporosis to take enough dietary nutrients, especially foods with a high bioavailable content of calcium. Dietary calcium, which is more absorbable and bioavailable, is essential when considering calcium requirements in the elderly due to the fact that the absorbability of calcium declines with age.

The inventors, after thorough investigation, have come up with the addition of γ-polyglutamic acid (γ-PGA, H form), γ-polyglutamate in Na$^+$ form, γ-polyglutamate in K$^+$ form, γ-polyglutamate in NH$_4^+$ form, γ-polyglutamate in Ca$^{++}$ form, or γ-polyglutamate in Mg$^{++}$ form, or a mixture thereof as a complex adsorbent for calcium and magnesium for improved solubility and bioavailability to enhance the absorption of calcium in the intestine. Foods are sometimes mineral-enriched using inorganic mineral salts or mineral powders, but these have the possibility of producing insoluble salts with other co-present substances. Since any excessive intake of one type of mineral may inhibit the adsorption of other minerals, there is not much improvement in the utilization of minerals in the body. A typical example is a large intake of calcium inhibits the absorption of iron. Also, excessive mineral enrichment in foods is disadvantageous in the taste of foods. Besides, it is generally considered that minerals must be present in the small intestine in a soluble state in order to be absorbed.

γ-Polyglutamic acid (γ-PGA, H form) and γ-polyglutamates (Na$^+$, K$^+$, NH$_4^+$, Ca$^{++}$, Mg$^{++}$ forms) possess good solubilizing effect on minerals in the lower small intestine and accelerate calcium absorption in a human body or an animal. Particularly, the present invention relates to a dietary product comprising γ-polyglutamic acid (γ-PGA, H form), γ-polyglutamate in Na$^+$ form, γ-polyglutamate in NH$_4^+$ form, γ-polyglutamate in K$^+$ form, γ-polyglutamate in Ca$^{++}$ form, or γ-polyglutamate in Mg$^{++}$ form, or a mixture thereof for use as a nutrition supplement.

In one embodiment of the present invention, the dietary product is a nutriment and comprises 0.005 wt. % to 100 wt. % of said nutrition supplement based on the total dry weight of said dietary product. In another embodiment, the dietary product is a food or feed composition and comprises 0.005 wt. % to 5 wt. % of said nutrition supplement based on the total dry weight of said dietary product.

The dietary product according to the present invention may further comprise a component selected from the group consisting of maltodextran with 5 to 40 dextrose equivalents, milk protein, soy protein isolate, glucose, lactose, sucrose, fructose, small chain oligo-fructose, glucan or other oligo-polysaccharide, collagen, hydrolyzed collagen gelatine, alpha-starch, hydrolyzed soy protein, partially hydrolyzed starch, glycerol, propylene glycol, ethanol, gum Arabic, guar gum, carrageneen, cellulose, and other modified cellulose and a mixture thereof. In addition, said dietary product can be in the form of a soft or hard gel capsule, a tablet, or a liquid preparation.

According to the present invention, the γ-polyglutamic acid (γ-PGA, H form), γ-polyglutamate in Na$^+$ form, γ-polyglutamate in K$^+$ form, γ-polyglutamate in NH$_4^+$ form, γ-polyglutamate in Ca$^{++}$ form, and γ-polyglutamate in Mg$^{++}$ form independently have a molecular weight ranging from 5000 to $2.5 \times 10^6$. We found that the γ-polyglutamic acid (γ-PGA, H form), γ-polyglutamate in Na$^+$ form, γ-polyglutamate in K$^+$ form, γ-polyglutamate in NH$_4^+$ form, γ-polyglutamate in Ca$^{++}$ form, and γ-polyglutamate in Mg$^{++}$ form independently having a molecular weight in the range from $150 \times 10^3$ to $450 \times 10^3$ daltons facilitate the growth of osteoblast cells in vitro study, and enhance the egg-layer performance and the growth of broiler chicken in vivo study.

Experimental Methods of the Invention

Commercial quantity of γ-polyglutamic acid (γ-PGA, H form) and its salts (i.e., γ-polyglutamate in Na$^+$ form, γ-polyglutamate in K$^+$ form, γ-polyglutamate in NH$_4^+$ form, γ-polyglutamate in Mg$^{++}$ form, and γ-polyglutamate in Ca$^{++}$ form) can be produced in a submerged fermentation process with *Bacillus subtilis*. *Bacillus subtilis* var. natto (see H. Kubota et al., Production of Poly(γ-Glutamic Acid) by *Bacillus subtilis* F-2-01, Biosci. Biotech. Biochem. 57(7), 1212-1213, 1993 and Y. Ogawa et. al., Efficient Production of γ-Polyglutamic Acid by *Bacillus subtilis* (natto) in Jar Fermentation, 61(10), 1684-1687, 1997), or *Bacillus licheniformis* (see JP 05-316999, published on 12 Mar. 1993) by using L-glutamic acid and glucose as main feed stocks. The microbial culture media contain carbon source, nitrogen source, inorganic minerals, and other nutrients. Usually, the amount of L-glutamic acid is used at a concentration ranging from 3 to 12%, glucose at a concentration of 5-12%, citric acid at a concentration of 0.2 to 2% are used as partial carbon source; peptone and ammonium sulfate or urea are used as nitrogen sources; yeast extract is used as nutrient source; $Mn^{++}$, $Mg^{++}$ and NaCl are used as mineral sources. Under proper aeration and agitation, the culture are maintained at temperatures from 30 to 40° C., and pH is maintained at 6-7.5 by using urea solution or sodium hydroxide solution; the culture time is normally continued for a period of 48 to 84 hours. γ-Polyglutamic acid (γ-PGA, H form) and its salts (i.e., γ-polyglutamate in $Na^+$ form, γ-polyglutamate in $K^+$ form, γ-polyglutamate in $NH_4^+$ form, γ-polyglutamate in $Mg^{++}$ form, and γ-polyglutamate in $Ca^{++}$ form) are accumulated extracellularly.

γ-Polyglutamic acid (γ-PGA, H form) and its salts (i.e., γ-polyglutamate in $Na^+$ form, γ-polyglutamate in $K^+$ form, γ-polyglutamate in $NH_4^+$ form, γ-polyglutamate in $Mg^{++}$ form, and γ-polyglutamate in $Ca^{++}$ form) are normally extracted from the fermentation broth by a series of procedure including, ultra-centrifugation, or pressurized filtration to separate cells, then adding 3-4 times of ethanol to precipitate out γ-polyglutamic acid (γ-PGA, H form) and its salts (i.e., γ-polyglutamate in $Na^+$ form, γ-polyglutamate in $K^+$ form, γ-polyglutamate in $NH_4^+$ form, γ-polyglutamate in $Mg^{++}$ form, and γ-polyglutamate in $Ca^{++}$ form). The precipitates are redissolved in water, and use another portion of ethanol to precipitate out γ-polyglutamic acid (γ-PGA, H form) and its salts (i.e., γ-polyglutamate in $Na^+$ form, γ-polyglutamate in $K^+$ form, γ-polyglutamate in $NH_4^+$ form, γ-polyglutamate in $Mg^{++}$ form, and γ-polyglutamate in $Ca^{++}$ form). The dissolution-precipitation steps are repeated several times in order to recover pure γ-polyglutamic acid (γ-PGA, H form) and its salts (i.e., γ-polyglutamate in $Na^+$ form, γ-polyglutamate in $K^+$ form, γ-polyglutamate in $NH_4^+$ form, γ-polyglutamate in $Mg^{++}$ form, and γ-polyglutamate in $Ca^{++}$ form).

γ-Polyglutamic acid (γ-PGA, H form) and its salts (i.e., γ-polyglutamate in $Na^+$ form, γ-polyglutamate in $K^+$ form, γ-polyglutamate in $NH_4^+$ form, γ-polyglutamate in $Mg^{++}$ form, and γ-polyglutamate in $Ca^{++}$ form) are normally dissolved in a proper solvent such as water, ethanol or methanol and pH is adjusted to 5.0 to 7.5. The properly selected multiple functional chemical cross-linking agents such as polyglycerol polyglycidyl ethers, sorbitol-based polyglycidyl ethers, polyethylene glycol diglycidyl ether, or trimethylolpropane triacrylate are added to the solution under constantly stirring, at a dose rate ranging from 0.01 to 20% of the weight of γ-polyglutamic acid (γ-PGA, H form) and its salts (i.e., γ-polyglutamate in $Na^+$ form, γ-polyglutamate in $K^+$ form, γ-polyglutamate in $NH_4^+$ form, γ-polyglutamate in $Mg^{++}$ form, and γ-polyglutamate in $Ca^{++}$ form), depending on the type of cross-linking agents and the quality of hydrogels required. The gelling reaction is normally completed within 1 to 4 hours at a reaction temperature from 50 to 120° C. depending on the equipment and conditions used. The hydrogels formed are then freeze-dried to produce dried cross-linked γ-polyglutamic acid (γ-PGA, H form) and its salts (i.e., γ-polyglutamate in $Na^+$ form, γ-polyglutamate in $K^+$ form, γ-polyglutamate in $NH_4^+$ form, γ-polyglutamate in $Mg^{++}$ form, and γ-polyglutamate in $Ca^{++}$ form), which possess super water absorption capacity, are non-water soluble, and form colorless, transparent and biodegradable hydrogels when fully swell in water.

γ-Polyglutamic acid (γ-PGA, H form) and its salts (i.e., γ-polyglutamate in $Na^+$ form, γ-polyglutamate in $K^+$ form, γ-polyglutamate in $NH_4^+$ form, γ-polyglutamate in $Mg^{++}$ form, and γ-polyglutamate in $Ca^{++}$ form) with a molecular weight ranging from 5,000 to 900,000 can be produced by controlled acidic-hydrolysis at a specific selected reaction conditions of pH, temperature, reaction time and concentration of γ-polyglutamic acid (γ-PGA, H form). The pH can be from pH 2.5 to 6.5 with proper acidulants such as HCl, $H_2SO_4$, or other organic acids, the hydrolysis temperature can be controlled in the range from 50 to 120° C., the reaction time from 0.5 to 5 hours, and the concentration of γ-polyglutamic acid (γ-PGA, H form) with molecular weight from $1\times10^6$ and higher can be any concentration as convenient as required. After the reaction is completed, further purification with dialysis or membrane filtration and drying are necessary to produce high purity small and middle molecular weight γ-polyglutamic acid (γ-PGA, H form) and its salts (i.e., γ-polyglutamate in $Na^+$ form, γ-polyglutamate in $K^+$ form, γ-polyglutamate in $NH_4^+$ form, γ-polyglutamate in $Mg^{++}$ form, and γ-polyglutamate in $Ca^{++}$ form) of choice. The acid-hydrolysis rate is faster at lower pH, higher temperature, and higher concentration of γ-polyglutamic acid (γ-PGA, H form). The γ-polyglutamate salts (i.e., γ-polyglutamate in $Na^+$ form, γ-polyglutamate in $K^+$ form, γ-polyglutamate in $NH_4^+$ form, γ-polyglutamate in $Mg^{++}$ form, and γ-polyglutamate in $Ca^{++}$ form) can be produced by reaction of selected γ-polyglutamic acid (γ-PGA, H form) with basic hydroxide solution or oxide of the metal ions of $Na^+$, $K^+$, $NH_4^+$, $Ca^{++}$, and $Mg^{++}$ of choice, and pH adjusted to desired condition from 5.0 to 7.2.as required.

EXPERIMENTAL EXAMPLE

In order to further explain this invention in detail, the experimental examples are presented in the following to show how this invention can be utilized to achieve the much improved calcium absorption and add health benefit to the growth and strength of bone, reduce calcium loss and reduce the osteoporosis condition. But the scope of this invention is not limited by these experimental examples.

Experimental Example 1

Cell Culture Study In Vitro—Facilitating the Growth of Osteoblast Cells

γ-Polyglutamic acid (γ-PGA, H form) HM with molecular weight of $980\times10^3$ daltons, γ-polyglutamate in $Na^+$ form HM with molecular weight of $880\times10^3$ daltons, and γ-polyglutamate in $Na^+$ form LM with molecular weight of $250\times10^3$ daltons were used in this study.

10 mg. of γ-polyglutamic acid (γ-PGA, H form) and/or γ-polyglutamate in $Na^+$ form, were added to 1 ml of F-12 DMEM (Dulbecco's Modified Eagle Medium) medium containing 10% fetal bovine serum (FBS), then a series of proper dilution were made to make different concentrations of γ-polyglutamic acid (γ-PGA, H form) and/or γ-polyglutamate in $Na^+$ form ranging from 0.1% to $4.9\times10^{-5}$% in the same nutrient medium were prepared, and 200 μl of each sample was deposited into 96-well culture plate in triplicate. The F-12 DMEM (Dulbecco's Modified Eagle Medium) medium containing only 10% fetal bovine serum (FBS) was used as control.

Sample of osteoblast cells from human bone marrow stem cells at their exponential growth phase was separated from the growth medium by centrifugation at 1200 rpm for 6 min., then washed three times with 10 ml of phosphate buffer solution (PBS) (0.01M phosphate, pH 7.4), and re-suspended in the F-12 DMEM medium containing 10% fetal bovine serum (FBS) to a cell density of $1\times10^5$/ml. Add 200 µl of the actively growing cell suspension to each sample well. The samples in the 96-well culture plate were well mixed with a vortex mixer then incubated for 48 hours at 34° C., RH 75% under 5% $CO_2$. Then, 20 µl of MTT [3-(4,5-dimethylthiazol-2-yl)-2,5-diphenol tetrazolium bromide] solution (1 mg/ml) was added to each well, mix well and re-incubated for 4 hours. A 100 µl of 10% SDS in 0.01N HCl buffer was added into each sample well to dissolve the crystal overnight at room temperature. The optical density ($OD_{570\ nm}$) of each sample well was measured and recorded for calculation of the osteoblast cell growth enhancement.

The dehydrogenase enzyme from midochondria of osteoblast cells can react with MTT salt, which is a colorless tetrazolium salt, to form a blue colored formazan salt crystal. The formazan crystal was then reacted with SDS and changed into soluble blue colored formazan. The intensity of blue formazan color represents the amount of growth of osteoblast cells. The enhancement in growth of osteoblast cells can be calculated as shown below:

$$\text{Increase in } MTT, \% = \frac{(OD_{570})a - (OD_{570})c}{(OD_{570})c} \times 100\%$$

Where, $(OD_{570})a$: the optical density of sample well, $(OD_{570})c$: the optical density of control well.

Experimental Example 2

The results of growth enhancement ratio from experimental example 1 were shown in Table 2 below:

TABLE 2

The growth enhancement ratio of osteoblast cells by different concentrations of γ-polyglutamic acid (γ-PGA, H form) and γ-polyglutamate in $Na^+$ form, as % of control

| Concentration % | γ-polyglutamate in $Na^+$ form HM, M.W. = $880 \times 10^3$ | γ-polyglutamate in $Na^+$ form LM, M.W. = $250 \times 10^3$ | γ-polyglutamic acid (γ-PGA, H form) HM, M.W. = $980 \times 10^3$ |
|---|---|---|---|
| 0.05 | 147.9 | 102.8 | 169.2 |
| 0.0125 | 135.9 | 96.9 | 142.8 |
| 0.0062 | 133.1 | 90.7 | 138.1 |
| 0.00039 | 131.0 | 80.0 | 125.3 |
| 0.000049 | 133.3 | 97.7 | 127.5 |

Note:
$(OD_{570})c = 0.713$ (=100%) for the control.

The results clearly showed that the growth of osteoblast cells was enhanced by over 130% with γ-polyglutamate in $Na^+$ form HM, over 80% with γ-polyglutamate in $Na^+$ form LM, and over 125% with γ-polyglutamic acid (γ-PGA, H form) HM, even at a low concentration level at 0.39 ppm. Higher molecular weight γ-polyglutamate in $Na^+$ form HM showed better growth enhancement.

Experimental Example 3

Cell Culture Study In Vitro—Facilitating the Bone Formation.

γ-Polyglutamic acid (γ-PGA, H form) HM with molecular weight of $980\times10^3$ daltons, γ-polyglutamate in $Na^+$ form HM with molecular weight of $880\times10^3$ daltons, and γ-polyglutamate in $Na^+$ form LM with molecular weight of $250\times10^3$ daltons were used in this study.

10 mg. of γ-polyglutamic acid (γ-PGA, H form) and/or γ-polyglutamate in $Na^+$ form, were added to 1 ml of F-12 DMEM (Dulbecco's Modified Eagle Medium) medium containing 10% fetal bovine serum (FBS), then a series of proper dilution were made to make different concentrations of γ-polyglutamic acid (γ-PGA, H form) and/or γ-polyglutamate in $Na^+$ form ranging from 0.1% to $3.1\times10^{-3}$% in the nutrient medium were prepared, and 1 ml of each sample was deposited into 6-well culture plate in triplicate. The F-12 DMEM (Dulbecco's Modified Eagle Medium) medium containing only 10% fetal bovine serum (FBS) was used as control.

2 ml of the F-12 DMEM (Dulbecco's Modified Eagle Medium) medium containing 10% fetal bovine serum (FBS) was added into each sample well, then mix well.

Sample of osteoblast cells from human bone marrow stem cells at their exponential growth phase was separated from the growth medium by centrifugation at 1200 rpm for 6 min. then washed three times with 10 ml of phosphate buffer solution (PBS) (0.01M phosphate, pH 7.4), and re-suspended in the F-12 DMEM medium containing 10% fetal bovine serum (FBS) to a cell density counts of about $1\times10^5$/ml. Add 1 ml of the actively growing cell suspension to each sample well. The samples in the 6-well culture plate were well mixed with a vortex mixer then incubated for 7 days at 34° C., RH 75% under 5% $CO_2$. Then, 200 µl of trypsin solution was added to each well and reacted for about 30 seconds at 34° C. Then, 1 ml of F-12 DMEM (Dulbecco's Modified Eagle Medium) medium was added into each sample well, and mix well. Suspended cells were withdrawn and discarded. 1 ml of 0.01M sodium bicarbonate/carbonate solution (pH 10) containing 100 µl of pNPP/2 ml (p-Nitrophenyl Phosphate solution (SK-5900, supplied by Vector) was added, mixed well and reacted for 30 minutes at room temperature, then add 1 ml of 0.1M NaOH solution to stop the reaction. The absorbance at 410 nm were measured and recorded.

Experimental Example 4

The results from experimental example 3 were tabulated in Table 3 as shown below.

TABLE 3

Effect on the bone formation as reflected by the activity of alkaline phosphatase, $OD_{410}$

| | Alkaline Phosphatase Activity, $OD_{410}$ | | |
|---|---|---|---|
| Concentration % | γ-polyglutamate in $Na^+$ form, HM M.W. = $880 \times 10^3$ 9 | γ-polyglutamate in $Na^+$ form, LM M.W. = $250 \times 10^3$ | γ-polyglutamate in $Na^+$ form, Hydrogel, 6% 2M |
| 0.1 | 1.25 | 1.27 | 1.64 |
| 0.05 | 1.53 | 1.02 | 1.63 |
| 0.025 | 1.33 | 1.04 | 1.66 |
| 0.0125 | 1.37 | 1.04 | 1.73 |
| 0.0062 | 1.43 | 1.05 | 1.74 |
| 0.0031 | 1.36 | 1.02 | 1.72 |
| 0.00 | 1.02 | 1.02 | 1.02 |

The alkaline phosphatase activity is an indicator of the existence of the osteoblast cells. High alkaline phosphatase activity presents before the calcification of cells, and the density of cells may regulate the osteoprogenitor differentiation and bone formation. When the human bone marrow stem cells were cultured for a week, the presence of any activity of alkaline phosphatase indicating the existence of osteoprogenitor cells (see Weinreb M., Schinar, D. M. and Rodan, G. A. 1990, Different Pattern of Alkaline Phosphatase, Osteodentin, and Osteocalcin Expression in Developing Rat Bone Visualized by in situ Hybridization, J. Bone Miner. Res. 5: 838-842; Yao, K. L., Todescan, R. Jr. and Sodek, J., 1994, Temporal Changes in Matrix Protein Synthesis and mRNA Expression during Mineralized Tissue Formation by Adult Rat Bone Marrow Cells in Culture. J. Bone Miner. Res. 9: 231-240; and Hesbertson A. and Aubin, J. E. 1995, Dexamethasone, Alters the Subpopulation Make-Up of Rat Bone Marror Stromal Cultures, J. Bone Miner. Res. 10: 285-294).

The results in Table 3 show that both γ-polyglutamate in $Na^+$ form HM and γ-polyglutamate in $Na^+$ form hydrogel are very effective in facilitating the growth of the osteoblast cells, the optimum concentration are 500 ppm (0.05%) and 6.2 ppm (0.0062%) for γ-polyglutamate in $Na^+$ form HM, and γ-polyglutamate in $Na^+$ form hydrogel, respectively. While the small molecular γ-polyglutamate in $Na^+$ form LM also facilitates the growth of osteoblst cells but at a much higher concentration level of 1000 ppm (0.1%). The results suggest that γ-polyglutamate in $Na^+$ form effectively facilitates the absorption of bioavailable calcium by the osteoblast cells and their precursors, and the strong hydrophilicity and active coil conformation of γ-polyglutamate in $Na^+$ form add in facilitating the functions of bone growth factors such as TGF-beta, activin, bone morphogenic protein (BMP), and bone sialoprotein (BSP) in the growth of bone by effectively complexing the bone growth factors and transport to the osteoblast cells for bone formation and growth.

Experimental Example 5

Field Feeding Studies In Vivo—Field Egg-Layer Feeding at a Local Yuan-An Chicken Farm.

Egg-layers of 73rd week old were used in this study. Total of 8 lots, and 8,000 chickens per lot were used. Egg samples were collected during 4-week period of regular feed (see Aho, P. W. 2002, Introduction to the US chicken meat industry, pages 801 to 818 in Commercial Chicken Meat and Egg Production, $5^{th}$ ed. Bell, D. D. and Weaver, junior, W. D., ed. Kluwer Publishing, Norwell, BS. Havenstein, G. B. et al., 1994, Growth, livability, and feed conversion of 1957 vs 1991 broilers when fed "typical" 1957 and 1991 broiler diets. Poult. Sci. 73: 1785-1794), followed by 4-week period of regular feed containing 100 ppm of γ-polyglutamate in $Na^+$ form LM with molecular weight ranging from 200×10³ to 400×10³, then 2-week period of regular feed. The egg samples were tested for the strength of egg shell; the thickness of egg shell; pH of egg-white and egg yolk; the heights of egg white. The HU values, which are a general fresh index or health index of the egg quality, were then calculated.

Experimental Example 6

The results from experimental example 5 were shown in Tables 4, 5, and 6.

TABLE 4

The effect of γ-polyglutamate in $Na^+$ form on the egg quality, HU Value

| Feeding | Sampling week | Test group HU value | Control group HU value | Difference in HU* value |
|---|---|---|---|---|
| Regular feed | 1-4 | 73.7 | 77.0 | 3.4 |
| Regular feed with 0.1% γ-polyglutamate in $Na^+$ form, LM | 5-8 | 70.9 | 71.9 | 1.0 |
| Regular feed | 9-10 | 67.9 | 71.0 | 3.2 |

TABLE 5

The effect of γ-polyglutamate in $Na^+$ form on the eggshell strength

| Feeding | Sampling week | Test group KGF value | Control group KGF value | Difference in KGF* value |
|---|---|---|---|---|
| Regular feed | 1-4 | 3.3 | 3.8 | 0.5 |
| Regular feed with 0.1% γ-polyglutamate in $Na^+$ form, LM | 5-8 | 3.3 | 3.4 | 0.1 |
| Regular feed | 9-10 | 3.5 | 3.7 | 0.2 |

Note:
1. $73^{rd}$ week old egg-layers were used.
2. 4 lots, and 8,000 chickens/lot were used
3. "*" for an average value of 10 eggs.
4. HU value is defined as following: HU = Haugh Unit - adjusted egg albumin height value = 100 * log (H – G * 0.5(30 * W * 0.37 – 100)/100 + 1.9 Where H - Albumin height in mm W - Weight of egg in gram G - 32.2, Gravitation constant
5. KGF - Eggshell strength unit

TABLE 6

The effect of γ-polyglutamate in $Na^+$ form on the height of egg white

| Feeding | Sampling week | Egg shell thickness mm* | Egg white height mm* | Egg yolk color | pH of Egg-white |
|---|---|---|---|---|---|
| Regular feed | 1-4 | 0.320 | 5.93 | 10.48 | 7.95 |
| Regular feed with 0.1% γ-polyglutamate in $Na^+$ form, LM | 5-8 | 0.327 | 6.00 | 10.90 | 7.91 |
| Regular feed | 9-10 | 0.330 | 5.45 | 10.50 | 7.93 |

The results in Tables 4, 5, and 6 showed that there are significant improvements in firming up of egg yolk and egg white, and egg shell strength, as shown in the reduced difference in HU and reduced difference in KGF values during the period of feeding containing γ-polyglutamate in $Na^+$ form. The egg shell thickness, egg white height, and egg yolk color are all improved during the period feeding containing γ-polyglutamate in $Na^+$ form.

Experimental Example 7

Field Feeding Study In Vivo—Field Pig Feeding at a Local Pig Farm at Yee-Thiang

The nutritional and health aspects of γ-polyglutamic acid (γ-PGA, H form), γ-polyglutamate in $Na^+$ form and γ-polyglutamate in $Ca^{++}$ form were studied in a field feeding to 2 sets of 2 groups of baby pigs, over a period of 39 days, at a level of 100 ppm of γ-polyglutamate in $Na^+$ form and γ-polyglutamate in $Ca^{++}$ form in feed supplement to the standard formulation. The results are shown in Table 7.

Experiment Example 8

The results from experimental example 7 are shown in Table 7.

TABLE 7

The effect of γ-polyglutamate in Na+ form and γ-polyglutamate in Ca++ form on the body fat of baby pigs

|  | Regular feed As control | Regular feed containing 0.1% γ-polyglutamate in Na+ form | Regular feed containing 0.1% γ-polyglutamate in Ca++ form |
|---|---|---|---|
| No. of pigs | 33 | 33 | 33 |
| Ave. starting weight, $W_1$ | 7.97 kgs | 7.82 kgs | 7.87 kgs |
| Ave. end weight, $W_2$ | 24.48 kgs | 23.57 kgs | 23.25 kgs |
| Ave. daily increase | 0.41 kgs | 0.41 kgs | 0.39 kgs |
| Ave. daily intake | 0.64 kgs | 0.62 kgs | 0.57 kgs |
| Ave. feed-to-meat | 1.52 kgs | 1.53 kgs | 1.45 kgs |
| Ave. $\Delta W = W_2 - W_1$ | 16.61 kgs | 15.75 kgs | 15.38 kgs |
| Ave. wt. Increase = $\Delta W/W_1$ | 2.07 kgs | 2.03 kgs | 1.95 kgs |

The results in Table 7 clearly show that γ-polyglutamate in Ca++ form has effect in reducing the body fat and reducing the feed-to-meat conversion for baby pigs, but γ-polyglutamate in Na+ form slightly increases the feed-to-meat conversion and negligible effect in reducing the body fat for the baby pigs.

Experimental Example 9

Field Feeding Study In Vivo—Field Broiler Feeding at a Local Chicken Farm at Tong San The nutritional and health aspects of γ-polyglutamate in Na+ form were studied in a field feeding to 2 sets of 4 groups of baby broilers, over a period of 25 days, at a level of 100 ppm of γ-polyglutamate in Na+ form LM, with molecular weight of $250 \times 10^3$, in feed supplement to the standard formulation. The results are shown in Table 8.

Experimental Example 10

The results from experimental example 9 are shown in Table 8.

TABLE 8

Effect of γ-polyglutamate in Na+ form on the growth of broiler

|  | Regular feed as Control | | Regular feed containing 0.1% γ-polyglutamate in Na+ form, LM | |
|---|---|---|---|---|
|  | Male* | Female* | Male* | Female* |
| No. of broiler | 461 | | 449 | |
| Ave. beginning wt. (kg), $W_1$ | 0.353 | | 0.365 | |
| Ave. end wt. (kg.). $W_2$ | 1.987 | | 2.085 | |
| Ave. feed consumption, kg | 2.915 | | 3.001 | |
| Feed conversion Rate, kg | 1.785 | | 1.747 | |
| Ave. $\Delta W = W_2 - W_1$ | 1.634 | | 1.720 | |
| Ave. $\Delta W/W_1$ | 4.629 | | 4.712 | |
| Wt. before slaughter, kg | 2.05 | 1.91 | 2.11 | 1.92 |
| Shank bone length, cm | 9.25 | 9.10 | 9.38 | 9.18 |
| Ash, shank bone, % | 43.2 | 42.9 | 44.6 | 44.9 |
| Calcium content, % | 17.40 | 16.34 | 17.66 | 16.69 |
| Phosphorus, % | 7.84 | 7.82 | 8.16 | 8.22 |

Note:
"*" means the average of 5 heads.

The results show that γ-polyglutamate in Na+ form facilitates the absorption of calcium and the overall weight of both male and female broilers. The average end weight per kg initial weight over a feeding period of 25 days are 4.712 kgs for those with regular feed (see Havenstein, G. B. et al., 1994, Growth, livability, and feed conversion of 1957 vs 1991 broilers when fed "typical" 1957 and 1991 broiler diets. Poult. Sci. 73: 1795-1794) containing γ-polyglutamate in Na+ form, and 4.629 kgs for those with regular feed (control). The shank bone lengths are 9.38 cm for male and 9.18 cm for female broilers in the test set of feed containing γ-polyglutamate in Na+ form, and 9.25 cm for male and 9.10 cm for female broilers in the control set with regular feed. Calcium contents in the shank bone are 17.66% for male and 16.69% for female broilers in the control set with regular feed.

Experimental Example 11

Cell Culture Study In Vitro—Facilitating GTF (Glucose Tolerance Factor) Activity by 3T3-L1 Cell Model Samples of γ-polyglutamate in Na+ form HM, with molecular weight of $880 \times 10^3$ and γ-polyglutamate in Na+ form LM, with molecular weight of $250 \times 10^3$ were used in this cell culture study.

Samples of 3T3-L1 pro-adipose cells were thawed and cultured in DMEM (Dulbecco's MEM) medium containing 10% fetal bovine serum (FBS) in an incubator at 37° C. under 5% $CO_2$ for a week before transferring to differentiation culture. After culturing for 2 days in the differentiation culture medium DMEM containing 10% FBS, 0.5 mM IBMX, 1 μM DX and 1 μg/ml insulin, the pre-adipose cells were transferred to the general DMEM medium containing 10% FBS and continuing culturing for another 10 days until more than 90% of cells transform into mature adipose cells. At this time, the cells change their shape from original star shapes into oily droplet shapes, which can be visually observed as white oily matters on the bottom of the culture plate. Until the cell differentiation is completed, then continue to the following experiment.

The mature adipose cells were first cultured in a sugar free DMEM medium containing 2% FBS in an incubator at 37° C. under 5% $CO_2$ for 1 hour, washed with PBS (0.01M phosphate buffer solution, pH 7.4), then adding 200 μl of test samples which containing different concentrations of γ-polyglutamate in Na+ form, and 200 μl of KBR solution containing 10 nM insulin and 2.5 g/l glucose, then incubated at 37° C. under 5% $CO_2$ for 2 hours. After centrifugation to separate the cells, the clear supernatant was taken for analyzing the concentration of glucose with a glucose analyzer. The difference in amount of glucose before and after the reaction is defined as the total glucose uptake by the adipose cells. The percentage of increase in glucose up-taken is defined as the GTF activity as shown in the following, $$\text{Increase in } GTF \text{ activity } (\%) = \frac{\text{Glucose uptake by the sample} - \text{Glucose uptake by the control}}{\text{Glucose uptake by the control}} \times 100\%$$

Eperimental Example 12

Figure 6:
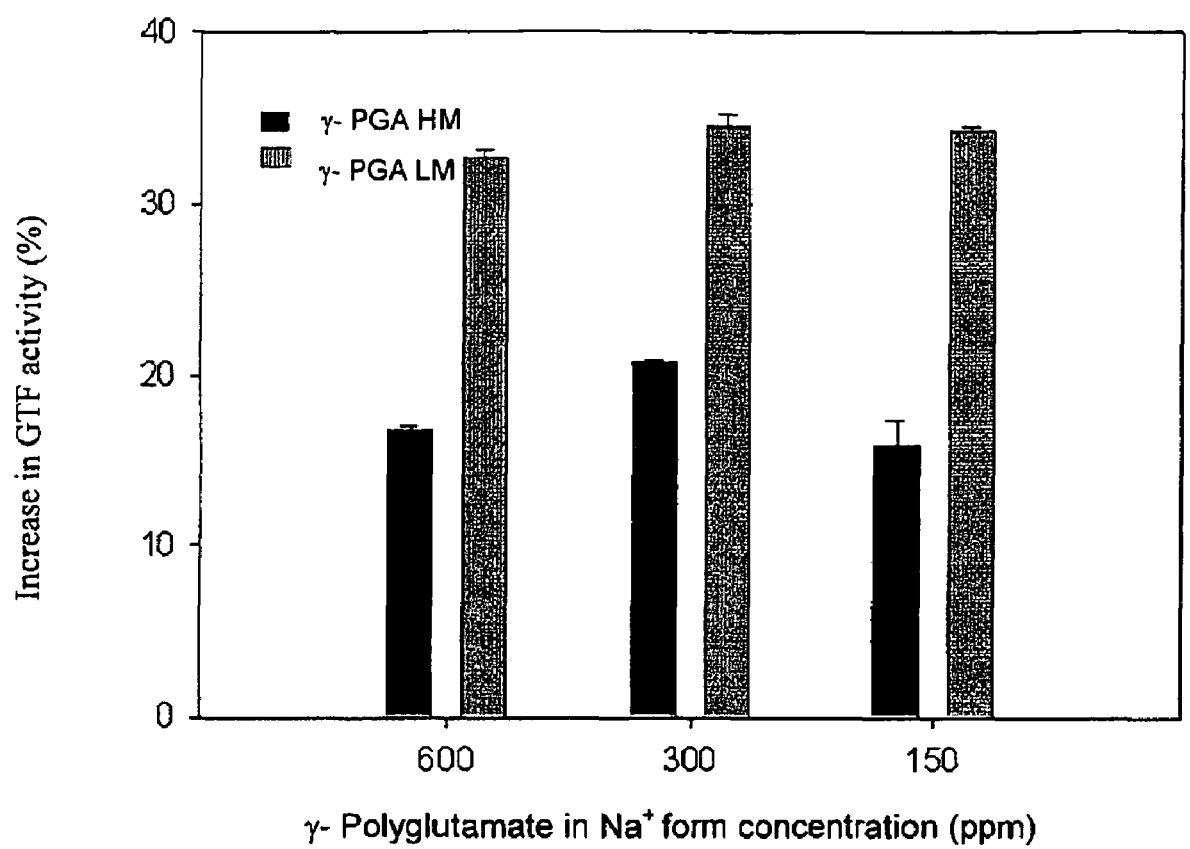
FIG. 6 shows the effect of different molecular weights of γ-polyglutamate in Na$^+$ form on the Glucose Tolerance Factor (GTF) activity exemplified in example 11.

The effect of different molecular weight of γ-polyglutamate in Na+ form on the GTF activity from experimental example 11 was shown in FIG. 6.

The results show both high and low molecular weights of γ-polyglutamate in $Na^+$ form effectively increased the GTF activity, with highest increase by 21% observed at about 300 ppm for the higher molecular weight of γ-polyglutamate in $Na^+$ form HM, and the highest GTF activity increase by about 33.5% observed at the concentration range from 150-600 ppm for the low molecular weight γ-polyglutamate in $Na^+$ form LM.

The results clearly suggest that γ-polyglutamate in $Na^+$ form facilitating the consumption of glucose by the GTF from adipose cells, which means more effective utilization of glucose in maintaining the growth and adding health benefits to the body, and may exert good biological functionality in controlling diabetes conditions in human.

The invention claimed is:

1. A dietary product comprising at least one nutrition supplement chosen from γ-polyglutamate hydrogels in $Na^+$ form, $K^+$ form, $NH_4^+$ form, $Ca^{++}$ form, $Mg^{++}$ form, or a mixture thereof, wherein said γ-polyglutamate hydrogel is prepared from γ-polyglutamate in $Na^+$ form, γ-polyglutamate in $K^+$ form, γ-polyglutamate in $NH_4^+$ form, γ-polyglutamate in $Mg^{++}$ form, γ-polyglutamate in $Ca^{++}$ form, or a mixture of two or more thereof cross-linked with one or more polyglycerol polyglycidyl ethers or sorbitol-based polyglycidyl ethers.

2. The dietary product of claim 1, which is a nutriment and comprises 0.005 wt. % to 100 wt. % of said nutrition supplement based on the total dry weight of said dietary product.

3. The dietary product of claim 1, which is a food or feed composition and comprises 0.005 wt. % to 5 wt. % of said nutrition supplement based on the total dry weight of said dietary product.

4. The dietary product of claim 1 further comprising at least one component chosen from a maltodextran comprising 5 to 40 dextrose equivalents, milk protein, soy protein isolate, glucose, lactose, sucrose, fructose, small chain oligo-fructose, glucan or other oligo-polysaccharide, collagen, hydrolyzed collagen gelatine, alpha-starch, hydrolyzed soy protein, partially hydrolyzed starch, glycerol, propylene glycol, ethanol, gum Arabic, guar gum, carrageneen, cellulose, other modified cellulose, and a mixture thereof.

5. The dietary product of claim 1, which is in a form of a soft gel capsule, a hard gel capsule, a tablet, or a liquid preparation.

6. The dietary product of claim 1 further comprising γ-polyglutamic acid (γ-PGA, H form), γ-polyglutamate in $Na^+$ form, γ-polyglutamate in $K^+$ form, γ-polyglutamate in $NH_4^+$ form, γ-polyglutamate in $Mg^{++}$ form, γ-polyglutamate in $Ca^{++}$ form, or a mixture thereof.

7. The dietary product of claim 6, wherein said γ-polyglutamic acid (γ-PGA, H form), γ-polyglutamate in $Na^+$ form, γ-polyglutamate in $K^+$ form, γ-polyglutamate in $NH_4^+$ form, γ-polyglutamate in $Mg^{++}$ form, and γ-polyglutamate in $Ca^{++}$ form independently have a molecular weight ranging from 5000 to $2.5 \times 10^6$ Da.

* * * * *